US006544788B2

(12) United States Patent
Singh

(10) Patent No.: US 6,544,788 B2
(45) Date of Patent: Apr. 8, 2003

(54) DISPOSABLE PERFUSION BIOREACTOR FOR CELL CULTURE

(76) Inventor: Vijay Singh, 391 Mt. Harmony Rd., Bernardsville, NJ (US) 07924

(*) Notice: Subject to any disclaimer, the term of this patent is extended or adjusted under 35 U.S.C. 154(b) by 0 days.

(21) Appl. No.: 09/784,568

(22) Filed: Feb. 15, 2001

(65) Prior Publication Data

US 2003/0036192 A1 Feb. 20, 2003

(51) Int. Cl.$^7$ .............................. C12N 5/00; C12M 1/12
(52) U.S. Cl. .................... 435/383; 435/394; 435/297.1; 435/297.2; 435/297.5; 435/818
(58) Field of Search ........................... 435/297.1, 297.2, 435/297.3, 297.4, 297.5, 304.1, 304.3, 818, 383, 394

(56) References Cited

U.S. PATENT DOCUMENTS

| | | | | |
|---|---|---|---|---|
| 5,057,429 A | * | 10/1991 | Watanabe et al. | 206/213.1 |
| 5,122,470 A | * | 6/1992 | Banes | 435/297.1 |
| 5,482,854 A | * | 1/1996 | O'Leary et al. | 215/229 |
| 5,523,228 A | * | 6/1996 | Ingram et al. | 435/297.1 |
| 5,672,505 A | * | 9/1997 | Jones et al. | 422/101 |
| 6,316,247 B1 | * | 11/2001 | Katz et al. | 210/446 |
| 6,319,706 B1 | * | 11/2001 | Kawaguchi et al. | 435/293.1 |

* cited by examiner

*Primary Examiner*—David A. Redding
(74) *Attorney, Agent, or Firm*—Ostrolenk, Faber, Gerb & Soffen, LLP

(57) ABSTRACT

A disposable bioreactor for perfusion cell culture. Cells are grown in a plastic bag that is rocked and aerated on a mechanical platform. The bioreactor bag contains a filter that allows liquid to be removed from the bioreactor-without losing cells. Nutrients may be added through another port. The perfusion filter is constructed such that it can move freely on the liquid surface. The filter is flicked rapidly across the surface as a result of the rocking motion of the bioreactor and this tangential motion of the filter keeps it from clogging. A weight-based control system regulates feed and harvest rates and allows weeks of continuous operation. This invention has numerous applications in biotechnology and medicine.

13 Claims, 6 Drawing Sheets

DISPOSABLE PERFUSION BIOREACTOR FOR CELL CULTURE

FIELD OF THE INVENTION

The present invention generally relates to systems and methods for culturing cells and more particularly to perfusion operations in a bioreactor. The invention has applications in the culture of animal, insect, and plant cells, for the production of secreted substances such as proteins, antibodies, polypeptides, and viruses. Applications include medical areas such as artificial organs and cell therapy.

BACKGROUND OF THE INVENTION

Cell culture has generated considerable interest in recent years due to the revolution in genetic engineering and biotechnology. Cells are cultured to make proteins, receptors, vaccines, and antibodies for therapy, research, and for diagnostics.

One limitation to the use of this technology is the high cost of operation. Traditionally, cell culture has been operated in a batch mode. In batch operation, the bioreactor is seeded with a small amount of cells and the cells are grown to high density. The cells secrete the product of interest and eventually die due to lack of nutrients at which point the culture is harvested. This method has several drawbacks—firstly, a large fraction of nutrients are wasted in simply growing up cells and are not used directly for making the product; secondly, product formation is often inhibited due to the buildup of toxic metabolic byproducts; and lastly critical nutrients are often depleted leading to low cell densities and consequently lower product yields.

It has long been recognized that perfusion culture offers better economics. In this operation, cells are retained in the bioreactor, and the product is continuously removed along with toxic metabolic byproducts. Feed, containing nutrients is continually added. This operation is capable of achieving high cell densities and more importantly, the cells can be maintained in a highly productive state for weeks. This achieves much higher yields and reduces the size of the bioreactor necessary. It is also a useful technique for cultivating primary or other slow growing cells. Perfusion operations have tremendous potential for growing the large number of cells needed for human cell and genetic therapy applications.

The central problem in perfusion culture is how to retain the cells in the bioreactor. Prior art can be classified into 3 basic separation technologies —1) filtration, 2) gravity sedimentation, and 3) centrifugation. Filtration methods require some means to keep the filter from clogging over the required weeks of operation. Cross-flow filters are typically used. Here a high tangential liquid velocity is used to keep the surface clean. Spinning filters are another embodiment of this concept. Gravity sedimentation can be used to separate the cells and several types of inclined settlers have been reported. The major problem with settlers is the varying sedimentation characteristics of different cells and the difficulty in scale-up to industrial systems. Centrifugation has found limited application in cell culture due to the difficulty in maintaining sterility.

All three current art methods share a common weakness—in that the liquid from the bioreactor must be pumped through the separation device and the cell-enriched material returned to the bioreactor. Keeping this recirculation loop sterile is difficult, and contamination often occurs. To maintain the high cross-flow velocity necessary to prevent clogging, the cells are subjected to high pumping shear in the recirculation loop and are often damaged. Oxygen depletion can also occur if the pumping rate is too slow. These factors often lead to degradation in product quality and quantity.

From this discussion of prior art, the limitations of current perfusion technology should be clear. As will be apparent in the following discussion, the present invention makes it possible to perform perfusion cell culture without a pump-around loop. This is due to the unique design of the cell retention filter and the rocking motion of the bioreactor.

SUMMARY OF THE INVENTION

The present invention solves the problem of filter clogging in perfusion bioreactors by a novel filter design coupled with a bioreactor based on wave-induced agitation. This bioreactor consists of a plastic bag that is partially filled with culture media and inflated to rigidity. The bioreactor is placed on a rocking platform that moves it back and forth through a preset angle and at a preset rocking rate. The rocking motion induces waves in the culture media promoting agitation and oxygen transfer, both essential to good bioreactor performance.

The perfusion filter is constructed such that it is neutrally buoyant with respect to the culture media. It is placed inside the bioreactor in such a manner so that it can move freely with the rocking motion. The bottom surface of the filter consists of a liquid permeable, but cell-retentive membrane. A flexible tube allows the essentially cell-free filtrate to be drawn out from inside the filter. As the bioreactor is rocked, the filter moves rapidly back and forth in the culture media. This back and forth motion serves to clean the filter and allows it to operate without clogging for weeks. Nutrient feed is pumped into the bioreactor and the harvest filtrate is removed continuously, or at periodic intervals.

The present invention provides an inexpensive cell culture bioreactor capable of perfusion operation. It does not require any external pumparound loop or recirculation pump. Thus, it is much simpler, has lower cost, and is less prone to contamination than conventional devices.

The perfusion bioreactor may be used to produce secreted products, produce large amounts of slow growing cells, or function as an artificial organ such as an extracorporeal liver. The simple construction and sterile design make it ideal for hospital use in cell and gene therapy applications.

BRIEF DESCRIPTION OF THE DRAWING(S)

For the purposes of illustrating the invention, there is shown in the drawings a form which is presently preferred, it being understood however, that the invention is not limited to the precise form shown by the drawing in which.

DETAILED DESCRIPTION OF EMBODIMENTS OF THE INVENTION

Figure 1:
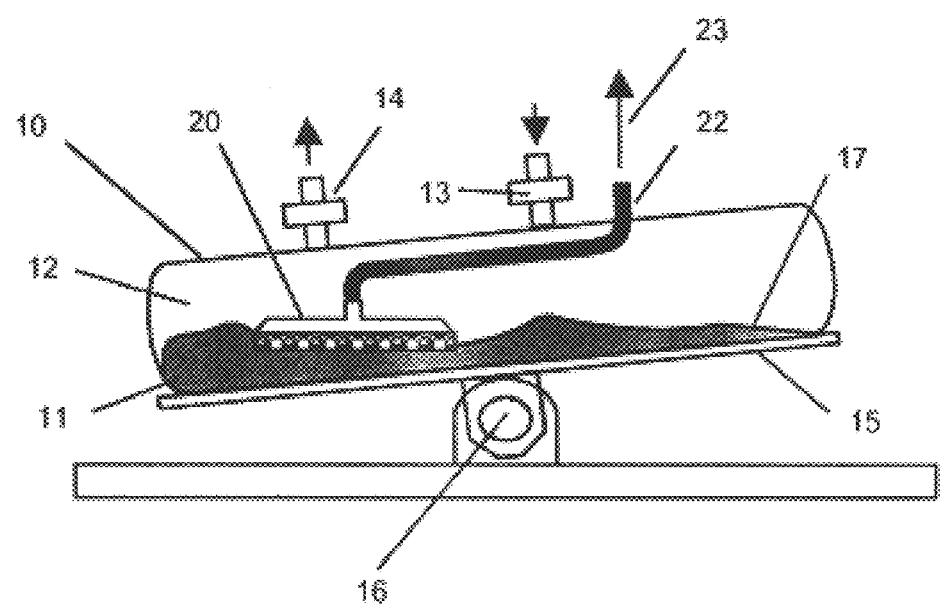
FIG. 1 is a cross-sectional view of the perfusion bioreactor.

As shown in FIG. 1, one embodiment of the perfusion bioreactor according to the present invention consists of a plastic bag 10 that is partially (10% to 80%) filled with culture media and cells 11. The remainder of the chamber is inflated and consists of gas filled headspace 12. Oxygen, necessary for cell metabolism, is provided by air (or other oxygen enriched gas) introduced through sterilizing inlet filter 13. Exhaust air is vented from the chamber through exhaust filter 14. This filter 13 ensures that no cells can be released as an aerosol from the bioreactor. It also ensures that in the event of bag depressurization, backflow through the vent 14 would not result in contamination. The bag 10 is attached to rocking platform 15 that moves back and forth across pivot point 16. Typical rocking speed is 10 to 30 rocks per minute through an angle of 4 to 10 degrees from the horizontal datum.

The perfusion filter 20 floats on the liquid surface 17. It is constructed such that it has essentially neutral buoyancy. The lower surface of the filter 20 consists of a liquid permeable membrane 21 that is submerged. This membrane 21 has a porosity such that cells cannot pass through it. By applying suction on the flexible filtrate tube 22, cell-free filtrate 23 is drawn up into the filter 20 and removed from the bioreactor. The flexible tube 22 is the only attachment point of the filter 20 and so the filter 20 is free to move on the liquid surface. The rocking motion of the bioreactor flicks the filter back and forth rapidly across the liquid surface 17. This rapid tangential movement of the filter 20 on the surface 17 exerts a scouring action and keeps the filter 20 from clogging.

Figure 2A:
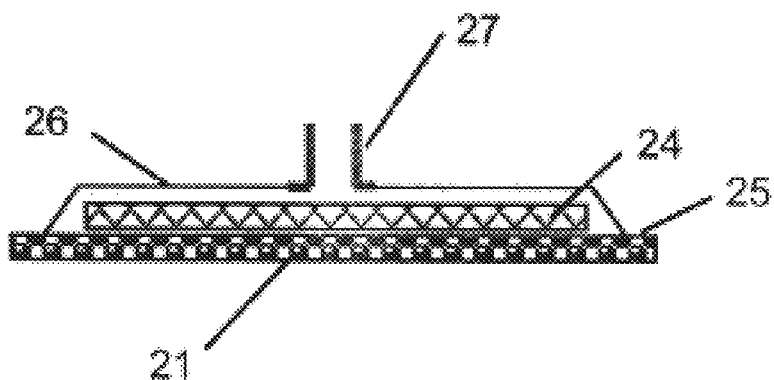
FIG. 2A is a cross-sectional view of the filter.
Figure 2B:
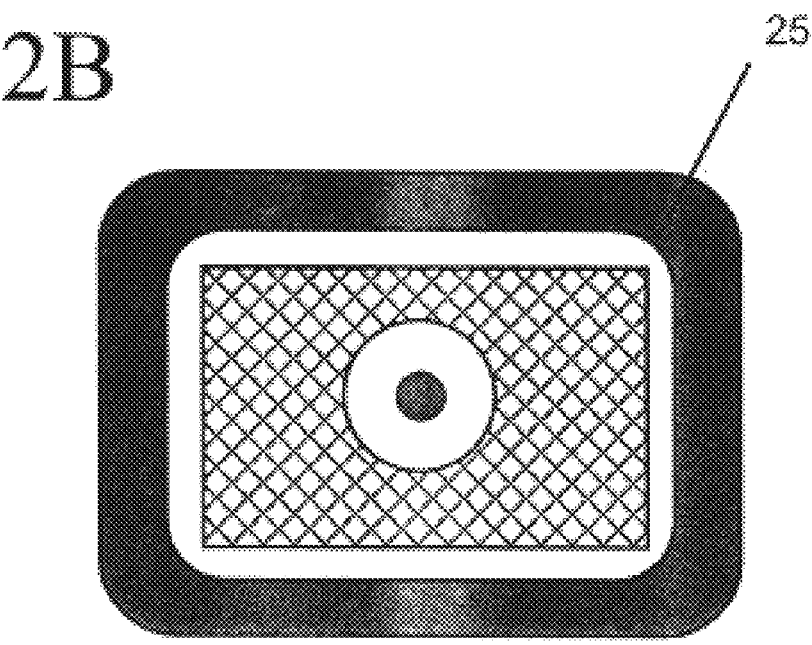
FIG. 2B is a top view of the filter.
Figure 3:
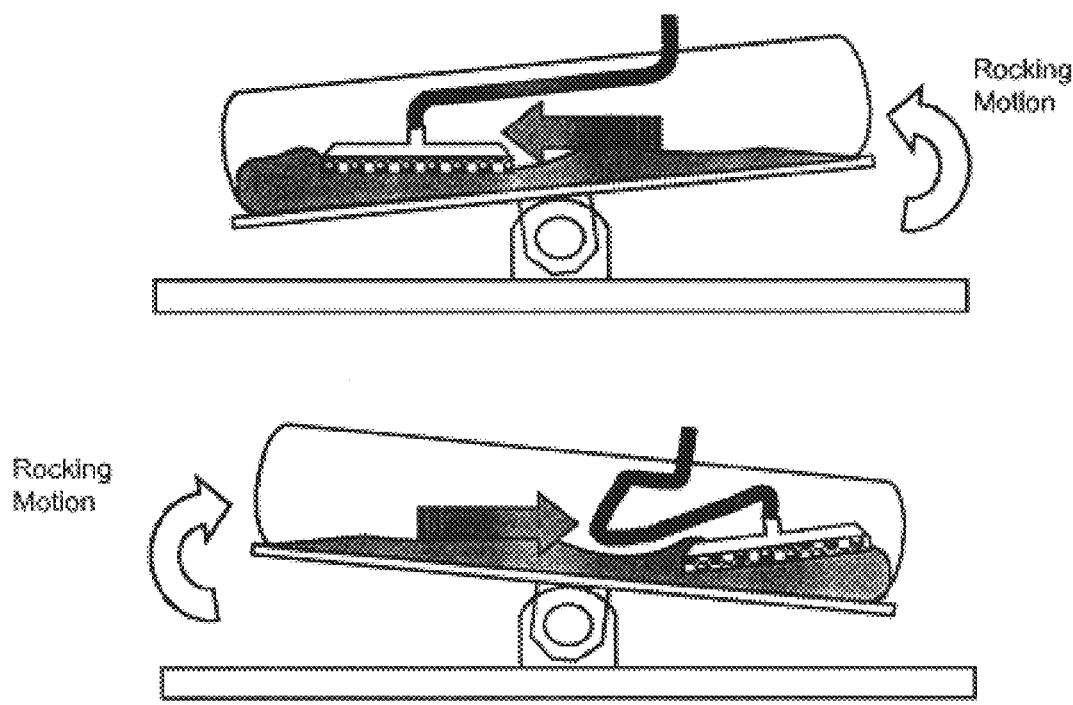
FIG. 3 is a schematic view of filter movement during operation of the bioreactor.

The perfusion filter 20 is constructed as shown in FIG. 2. The filtration membrane 21 is made of a material of suitable porosity to retain cells. In the preferred embodiment, the filter membrane 21 is a sintered porous polyethylene sheet with a mean pore size of 7 microns (Porex T3 ). The porous polyethylene has the advantage of a very smooth surface and is electrically charged such that the cells are inhibited from attaching to the surface of the filter 20. The polypropylene material can also be easily heat welded. Other suitable plastics such as nylon and polyethylene could also be used. The filtration membrane 21 is heat welded to a non-porous upper layer 26. In the preferred embodiment this layer 26 is made of clear polyethylene film. A hose barb port 27 is attached to the upper layer 26 so that the filtrate tube 22 (FIG. 1) may be easily attached. A polyethylene mesh 24 is placed inside the filter 20 to prevent the filtration membrane 21 from being sucked flat against the upper layer 26 and choking off flow. The entire filter assembly 20 is sealed by a thermally welded seam 25.

The filter 20 is placed inside the bioreactor bag and the harvest tube 22 (FIG. 1) is connected using flexible tubing so that the filtrate can be removed from the bioreactor. It is preferable that this tubing be flexible enough to permit the filter 20 to move freely on the liquid surface 17. The filter 20 and bioreactor bag 10 is sterilized in situ by gamma radiation. The system is extremely simple to use—the bag 10 is filled with growth promoting sterile nutrient media. Cells are added and the bag 10 is placed on the rocking platform 15. The bioreactor is rocked and aerated to promote cell growth. Once the cell density has reached the desired level (typically 2 to 4 million cells/ml) perfusion operation is started. Cell-free filtrate is withdrawn through the perfusion filter 20 and collected. Equal amount of feed is added to provide nutrients. The perfusion operation puts the cells into a steady-state operation and can be extended for many weeks. Perfusion operations require that nutrients be fed at a slow rate to the bioreactor. At the same time, liquid must be removed from the bioreactor to keep the volume reasonably constant and to remove toxic metabolic byproducts. In the case of secreted products, this harvest liquid may contain the product to be purified. In perfusion operation it is critical that cells not be allowed to leave the bioreactor. Otherwise, the cell concentration in the bioreactor will drop due to washout of the cells. In practice, a small amount of cell loss (<10%) is tolerated in order to remove dead and dying cells and to promote a low level of cell regrowth.

For the perfusion device to function continuously for long periods of time it is necessary to control the volume in the reactor. It is essential that the feed and harvest be controlled such that the volume in the bioreactor remains constant. In conventional tank-type bioreactors, volume control is achieved by controlling the filtrate flow rate so as to maintain a constant liquid level in the bag 10. In the present invention, the flexible bag 10 does not permit accurate level measurement so an alternate method of controlling the volume had to be devised.

Figure 4:
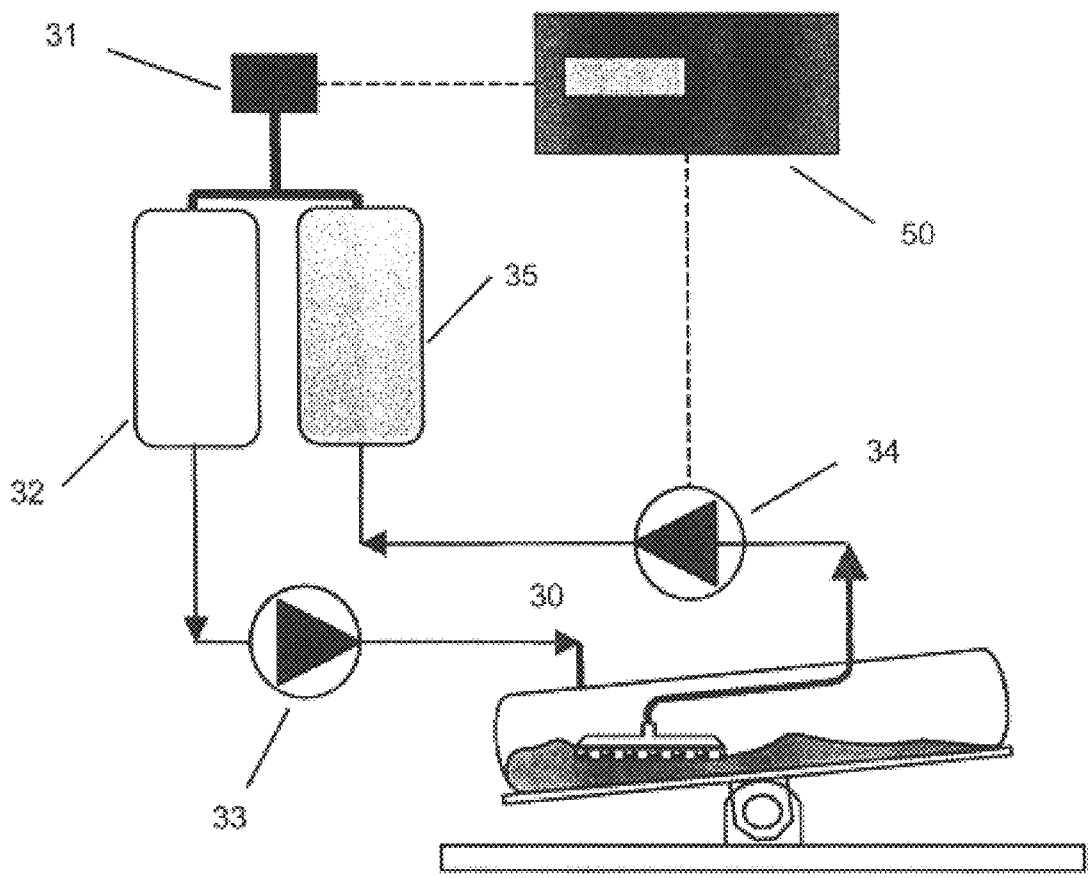
FIG. 4 is a schematic of the perfusion flow control circuit.

The perfusion control system according to the present invention is shown in FIG. 4. The bioreactor described earlier is fed nutrients from a feed container 32 that is suspended from a hook equipped with a weight sensor 31. The rate of feed is controlled by feed pump 33. This feed pump 33 is operated intermittently by controller 50 pumping feed into the bioreactor via inlet port 30. The controller 50 turns the feed pump 33 on until preset weight of feed, as measured by loss in weight of the feed container 32, is delivered into the bioreactor. Next, the harvest pump 34 is switched on. This pump 34 sucks filtrate up through the perfusion filter 20 and pumps it into a collection vessel 35 also suspended from the same hook as the feed container 32. The controller 50 runs this pump 34 until the net weight loss measured at the hook is zero. This ensures that the amount of harvest removed equals the feed added to the bioreactor. The cycle is then repeated. The frequency of cycling can be adjusted to give the desired overall perfusion rate. The cumulative amount of feed added and harvest removed can be easily calculated from the cycling of the weight sensor 31. This simple mechanism provides complete control of feed rate and harvest. Alarms can be programmed to warn of pump or filter failure to prevent the loss of valuable cells.

EXAMPLES

Example 1

Growth of Hybridoma Cells

Hybridoma cells were grown in convention batch culture and in the perfusion culture bag that is the subject if this invention. These cells produce a monoclonal antibody for therapeutic use. The culture media used was Becton-Dickenson CeliMab medium with 10% fetal calf serum and 1% pluronic F-68. Cultivation was performed in a Wave Bioreactor® SYSTEM20 benchtop unit with integral temperature and CO2 control. Two Cellbag® 2L bag bioreactors were run simultaneously using inoculum pooled from five T-175 flasks. One Cellbag was run as a batch culture, the other, equipped with a filter as described in this invention was operated in perfusion mode. Operating parameters are shown in Table 1.

TABLE 1

| Experimental Parameters | |
|---|---|
| Sampling | Cell density, pH, glucose and lactate concentrations were determined daily. |
| Agitation | Rocking rate was started at 8 rpm and the increased by 2 rpm per day up to a maximum of 35 rpm. |
| Aeration | 5% CO2 overlay. O2 was increased based on dilution rate to maximum of 50% O2. |
| Batch operation | Initial volume 300 ml + 300 ml + 400 ml (final volume 1 liter) |

TABLE 1-continued

Experimental Parameters

| | |
|---|---|
| Perfusion operation | Initial volume 500 ml + 500 ml (total 1 liter) - then start perfusion once cell density >2 × 10$^6$ cells/ml. Initial dilution rate was 0.2/day. Dilution rate was adjusted to keep glucose/lactate concentrations constant. |

Figure 5:
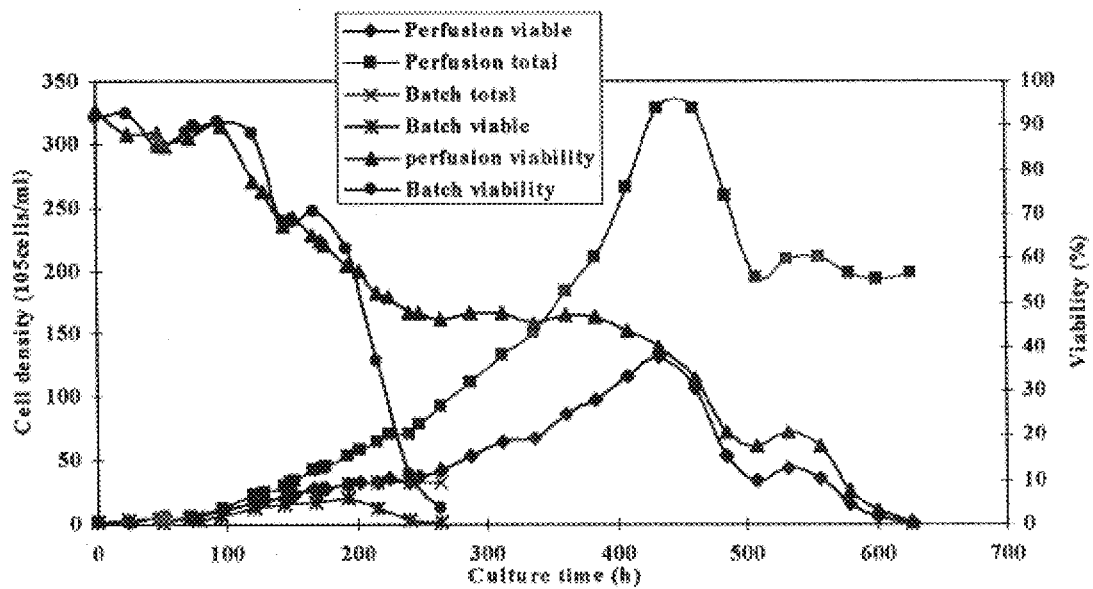
FIG. 5 is an example growth profile comparing perfusion operation to batch culture.

FIG. 5 shows the time-profile of cell density and viability for batch and perfusion cultures. For the batch culture, the maximum cell density peaked at 3×10$^6$ cells/ml and after 9 days the viability declined rapidly. In contrast, in the perfusion culture, the cells continued to grow and the maximum cell density was 32×10$^6$ cells/ml. Viability decreased slowly towards the middle of the run and stabilized at around 50% for over 10 days. These results show that: 1) the perfusion bioreactor can support 10×cell density;2) can maintain high viability for extended time and 3) can operate without clogging or losing a significant number of cells over weeks of operation.

Figure 6:
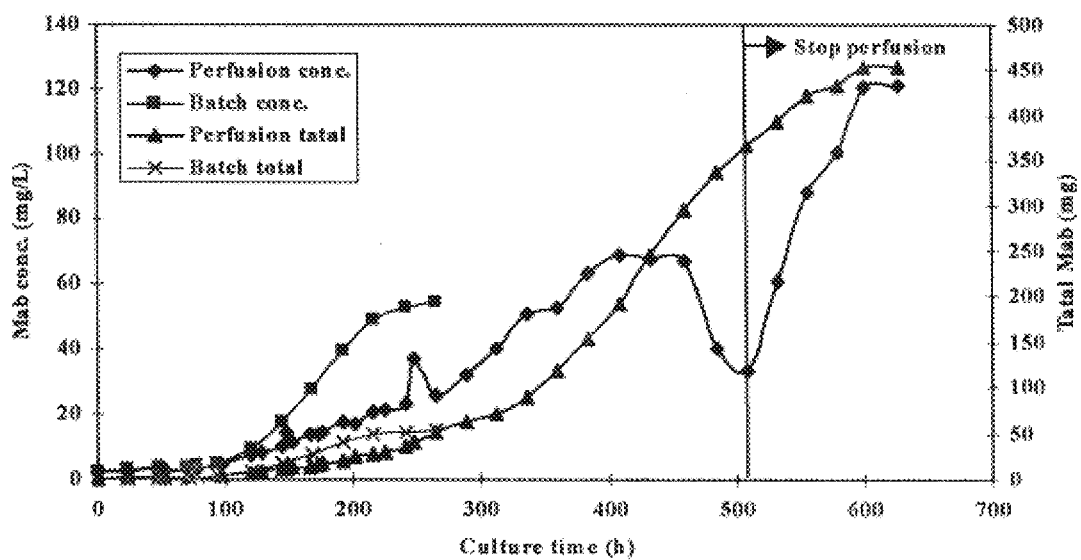
FIG. 6 is an example monoclonal antibody production profile compared to batch culture.

FIG. 6 shows the corresponding monoclonal antibody (Mab) concentration and total Mab production for the batch and perfusion cultures. The perfusion culture produced twice the Mab concentration as the batch operation and cumulative production was 450 mg. This was nine-fold higher than an equivalent batch culture. Table 2 summarizes the cost and performance data normalized on the basis of 10 liters of media consumed.

TABLE 2

Mab production Wave Bioreactor - 1 liter culture volume

| | Batch | Perfusion |
|---|---|---|
| Culture time | 12 days | 25 days |
| Reactor Cost | $150 | $170 |
| Mab Production/reactor (mg) | 54.4 | 450 |
| Production cost $mg of Mab | 5.51 | 2.29 |
| Mg of Mab/10 L medium | 544 | 450 |
| mg of Mab/day | 4.5 | 18.2 |

This example demonstrates the capability of the present invention to perform without clogging for over 25 days. Similar results have been obtained with larger systems of 10 and 100 liter culture volume. The technology does not appear to be limited by scale.

Example 2

Growth of Human T-cells

T-cells harvested from pedriatic cancer patients were introduced along with growth promoting media into a perfusion culture bag that is the subject of this invention. Cells were grown until a density of 2 million cells/ml was reached at which point perfusion operations were started. Cultivation was continued for over two weeks at which point the cell density was well over 20 million cells/ml. The cultivated cells were harvested and concentrated by centrifugation and administered to the donor patient. The ex vivo expanded cells eliminated the need for bone marrow transfusion, thereby reducing the need for suitable donors and the risk of adventitious contamination. The perfusion equipped bioreactor allowed efficient cultivation of these cells in an environment specific to each patient and free for potential contamination.

Although the invention has been described in terms of specific embodiments and applications, persons skilled in the art, can in light of this teaching, generate additional embodiments without exceeding the scope or departing from the spirit of the claimed invention. The specific composition of the various elements of the perfusion bioreactor system, for example, should not be construed as a limiting factor. Accordingly, it is to be understood that the drawings and descriptions in this disclosure are proffered to facilitate comprehension of the invention and should not be construed to limit the scope thereof.

What is claimed is:

1. A bioreactor assembly comprising:
   a chamber capable of receiving a liquid media; and
   a filter disposed in the chamber, the filter being free to move within the chamber, wherein the liquid media has a surface when received in the chamber, and wherein the filter is constructed to be disposed on the surface of the liquid media.

2. A bioreactor assembly comprising:
   a chamber capable of receiving a liquid media; and
   a filter disposed in the chamber, the filter being free to move within the chamber, wherein the chamber is a flexible bag.

3. A bioreactor assembly comprising:
   a chamber capable of receiving a liquid media; and
   a filter disposed in the chamber, the filter being free to move within the chamber, further comprising: a rocking platform on which the chamber is located, whereby rocking of the rocking platform induces the wave motion in the liquid media received in the chamber.

4. The bioreactor assembly as recited in claim 1, wherein the chamber has at least a first outlet, the bioreactor further comprising a harvest tube coupled to the filter and coupled to the first outlet.

5. The bioreactor assembly as recited in claim 1, further comprising a control system coupled to the chamber, wherein the control system controls the volume of the liquid media in the chamber.

6. The bioreactor assembly as recited in claim 5, wherein the chamber has an inlet port and an outlet port, the control system further comprising:
   a weight sensor;
   a feed container coupled to the weight sensor and coupled to the inlet port, the feed container capable of receiving a feed liquid;
   a feed pump coupled to the feed container;
   a collection container coupled to the weight sensor and coupled to the outlet port; and
   a controller coupled to the weight sensor and coupled to the feed pump, wherein the controller activates feed pump to pump the feed liquid from the feed container to the chamber when the weight sensor indicated an imbalance.

7. The bioreactor assembly as recited in claim 1, wherein the filter further comprises:
   an upper layer; and
   a filtration membrane coupled to the upper layer.

8. The bioreactor assembly as recited in claim 7, wherein the filtration membrane is coupled to the upper layer by heat welding.

9. The bioreactor assembly as recited in claim 7, wherein the filtration membrane is a porous plastic sheet.

10. The bioreactor assembly as recited in claim 9, wherein the porous plastic sheet is a polyethylene sheet.

11. The bioreactor assembly as recited in claim 7, further comprising a mesh disposed between the upper layer and the filtration membrane.

12. A bioreactor assembly comprising:

a chamber, the chamber having an outlet port;

a harvest tube disposed in the chamber and coupled to the outlet port;

a filter disposed in the chamber and coupled only to the harvest tube, whereby the filter moves within the chamber, wherein the chamber further has an inlet port, and wherein the chamber is capable of containing a liquid media, the bioreactor assembly further comprising:

a weight sensor;

a feed container coupled the weight sensor and coupled to the inlet port, the feed container capable of receiving a feed liquid;

a feed pump coupled to the feed container a collection container coupled to the weight sensor and coupled to the outlet port; a collector pump coupled to the collection container, wherein the collector pump pumps the liquid media from the chamber into the collection container; and a controller coupled to the weight sensor and coupled to the feed pump, wherein the controller activates feed pump to pump the feed liquid from the feed container to the chamber when the weight sensor indicated an imbalance, whereby the volume of the liquid media in the chamber stays substantially constant.

13. A method of operating a bioreactor comprising:

disposing a filter in a chamber, wherein the filter is free to move about the interior of the chamber;

at least partially filling the chamber with a liquid media; and rocking the chamber thereby inducing a wave motion in the liquid media, whereby the wave motion moves the filter and serves to prevent clogging of the filter.

* * * * *